(12) United States Patent
Wen et al.

(10) Patent No.: US 11,992,306 B2
(45) Date of Patent: May 28, 2024

(54) TEMPERATURE MONITORING FOR SLEEP DISORDERED BREATHING

(71) Applicant: Cardiac Pacemakers, Inc., St. Paul, MN (US)

(72) Inventors: Gezheng Wen, Shoreview, MN (US); Pramodsingh Hirasingh Thakur, Woodbury, MN (US); John D. Hatlestad, Maplewood, MN (US); Qi An, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 207 days.

(21) Appl. No.: 17/486,521

(22) Filed: Sep. 27, 2021

(65) Prior Publication Data

US 2022/0095953 A1   Mar. 31, 2022

Related U.S. Application Data

(60) Provisional application No. 63/085,889, filed on Sep. 30, 2020.

(51) Int. Cl.
*A61B 5/08* (2006.01)
*A61B 5/00* (2006.01)
(Continued)

(52) U.S. Cl.
CPC .............. *A61B 5/0826* (2013.01); *A61B 5/01* (2013.01); *A61B 5/085* (2013.01); *A61B 5/091* (2013.01);
(Continued)

(58) Field of Classification Search
CPC ... A61B 5/4806; A61B 5/0826; A61B 5/4818; A61B 5/4809; A61B 5/4815; A61B 5/686; A61B 5/0031; A61B 5/01; A61B 5/085
See application file for complete search history.

(56) References Cited

U.S. PATENT DOCUMENTS 6,964,641 B2   11/2005  Cho et al.
7,469,697 B2   12/2008  Lee et al.
(Continued)

FOREIGN PATENT DOCUMENTS

CN   116194041 A   5/2023
EP      2008581 A2   12/2008
(Continued)

OTHER PUBLICATIONS

Martinez-Nicolas, Antonio, et al., "Circadian Impairment of Distal Skin Temperature Rhythm in Patients With Sleep-Disordered Breathing: The Effect of CPAP", Sleep, vol. 40, No. 6, 2017, 11 pgs.
(Continued)

*Primary Examiner* — Eric F Winakur
*Assistant Examiner* — Elina Sohyun Ahn
(74) *Attorney, Agent, or Firm* — Schwegman Lundberg & Woessner, P.A.

(57) ABSTRACT

Systems and methods to are disclosed to determine a sleep disordered breathing parameter of a patient, including receiving respiration information of the patient and temperature information of the patient and to determine the sleep disordered breathing parameter of the patient using the received respiration information and temperature information of the patient.

22 Claims, 5 Drawing Sheets

(51) Int. Cl.
  *A61B 5/01* (2006.01)
  *A61B 5/085* (2006.01)
  *A61B 5/091* (2006.01)

(52) U.S. Cl.
  CPC ............ *A61B 5/4806* (2013.01); *A61B 5/686* (2013.01); *A61B 5/746* (2013.01); *A61B 2562/0271* (2013.01)

(56) References Cited

U.S. PATENT DOCUMENTS

| | | |
|---|---|---|
| 2005/0197588 A1 | 9/2005 | Freeberg |
| 2007/0123758 A1* | 5/2007 | Miesel ............... A61N 1/36067 607/2 |
| 2007/0150006 A1 | 6/2007 | Libbus et al. |
| 2010/0324438 A1* | 12/2010 | Ni ........................ A61B 5/4818 600/529 |
| 2018/0117316 A1* | 5/2018 | Wagner ................ A61N 1/3601 |

FOREIGN PATENT DOCUMENTS

| | | |
|---|---|---|
| WO | WO-2009036327 A1 | 3/2009 |
| WO | WO-2017106840 A1 | 6/2017 |
| WO | WO-2018068084 A1 | 4/2018 |
| WO | WO-2022072278 A1 | 4/2022 |

OTHER PUBLICATIONS

Simms, Taryn, et al., "Differential Timing of Arousals in Obstructive and Central Sleep Apnea in Patients with Heart Failure", Journal of Clinical Sleep Medicine, vol. 9, No. 8, 2013, pp. 773-779.

"International Application Serial No. PCT/US2021/052201, International Preliminary Report on Patentability dated Apr. 13, 2023", 9 pgs.

"International Application Serial No. PCT/US2021/052201, International Search Report dated Jan. 31, 2022", 7 pgs.

"International Application Serial No. PCT/US2021/052201, Written Opinion dated Jan. 31, 2022", 7 pgs.

* cited by examiner

TEMPERATURE MONITORING FOR SLEEP DISORDERED BREATHING

CLAIM OF PRIORITY

This application claims the benefit of priority of U.S. Provisional Patent Application Ser. No. 63/085,889, filed on Sep. 30, 2020, which is herein incorporated by reference in its entirety.

TECHNICAL FIELD

This document relates generally to monitoring sleep disordered breathing, and more particularly, but not by way of limitation, to systems and methods for temperature monitoring for sleep disordered breathing.

BACKGROUND

Ambulatory medical devices (AMDs) include implantable, wearable, external, or one or more other type of medical devices having sensors configured to sense physiologic signals from a patient. Detected physiologic signals can be used to determine or monitor patient status or condition. Frequent patient monitoring, such as using one or more AMDs, can enable early detection of worsening patient condition or identification of patients or groups of patients having elevated risk of future adverse events, including hospitalization. Early detection of worsening patient condition can prevent or reduce patient hospitalization. Identifying and safely managing patient risk of worsening condition may reduce patient hospitalizations, the amount or severity of medical interventions, and overall healthcare costs.

Sleep disordered breathing (SDB) describes a group of chronic conditions characterized by abnormal or insufficient breathing during sleep, ranging from snoring or a partial cessation of breathing to sleep apnea, a temporary cessation of breathing during sleep. Typical SDB symptoms include loud snoring or difficulty breathing during sleep, including brief periods without breathing followed by gasping or snorting, night sweats, or waking often to use the lavatory during sleep. SDB patients often suffer from daytime sleepiness and fatigue, poor concentration and memory, and reduced quality of life. Further, SDB is a common but often undiagnosed comorbidity in heart failure (HF) patients or patients with cardiovascular disease. SDB is classified itself as a disease once sleep apnea is confirmed.

There are two main types of sleep apnea: obstructive sleep apnea (OSA) and central sleep apnea (CSA). OSA is a complete or partial blockage of the upper airway during sleep, often occurring when the muscles of the back of the throat relax, causing the complete or partial blockage of a patient airway, requiring chest muscles and diaphragm of the patient to work harder to force air through the blocked airway. CSA is a cessation of ventilation, often repetitive, not due to a blockage of the airway, but due to a lack of ventilatory effort, where a patient's brain fails to transmit the proper signals to the breathing muscles.

Other forms of SDB include hypopnea, characterized by abnormally shallow or slow breathing, and Cheyne-Stokes respiration, an abnormal breathing pattern including periods of progressively deeper, then shallower breathing sometimes resulting in a temporary cessation.

SUMMARY

Systems and methods to are disclosed to determine a sleep disordered breathing parameter of a patient, including receiving respiration information of the patient and temperature information of the patient and to determine the sleep disordered breathing parameter of the patient using the received respiration information and temperature information of the patient.

An example (e.g., "Example 1") of subject matter (e.g., a system) may comprise: means for receiving respiration information of a patient and temperature information of the patient; and means for determining a sleep disordered breathing parameter of the patient using the received respiration information and temperature information of the patient.

In Example 2, the subject matter of Example 1 may optionally be configured such that the means for receiving respiration information comprises a signal receiver circuit configured to receive respiration information of the patient and temperature information of the patient and the means for determining the sleep disordered breathing parameter comprises an assessment circuit configured to determine the sleep disordered breathing parameter of the patient using the received respiration information and the received temperature information of the patient.

In Example 3, the subject matter of any one or more of Examples 1-2 may optionally be configured such that the respiration information comprises impedance information of the patient indicative of a tidal volume of the patient and the assessment circuit is configured to determine the sleep disordered breathing parameter using a detected decrease in the received impedance information from a baseline respiration measure over a detection window, the decrease greater than a sleep disordered breathing threshold.

In Example 4, the subject matter of any one or more of Examples 1-3 may optionally be configured such that the temperature information comprises a temperature of an implantable housing of the medical device system indicative of distal skin temperature of the patient and the assessment circuit is configured to determine the sleep disordered breathing parameter using a combination of the received impedance information over the detection window and the temperature of the implantable housing corresponding to the detection window.

In Example 5, the subject matter of any one or more of Examples 1-4 may optionally be configured such that the assessment circuit is configured to determine the sleep disordered breathing parameter using the detected decrease in the received impedance information indicative of the tidal volume of the patient greater than the sleep disordered breathing threshold and the temperature of the implantable housing greater than a temperature threshold, the sleep disordered breathing parameter includes an indication that a sleep disordered breathing event has occurred over the detection window, and the assessment circuit is configured to determine the baseline tidal volume measure using the determined tidal volume measure of the patient over a baseline period longer than the detection window and preceding the detection window.

In Example 6, the subject matter of any one or more of Examples 1-5 may optionally be configured such that the detection window has a period between 5 and 15 seconds, the baseline period is a minute or longer.

In Example 7, the subject matter of any one or more of Examples 1-6 may optionally be configured such that the assessment circuit is configured to count a number of sleep disordered breathing events in a daily period.

In Example 8, the subject matter of any one or more of Examples 1-7 may optionally be configured such that the assessment circuit is configured to adjust at least one of the sleep disordered breathing threshold or the length of the detection window using the received temperature information.

In Example 9, the subject matter of any one or more of Examples 1-8 may optionally be configured such that the assessment circuit is configured to: determine an initial sleep disordered breathing parameter of the patient using the received respiration information; and determine a confidence indication of the determined initial sleep disordered breathing parameter using the received temperature information.

In Example 10, the subject matter of any one or more of Examples 1-9 may optionally be configured such that the confidence indication includes indications of high confidence and low confidence and the assessment circuit is configured to: determine an indication of high confidence if the received temperature information corresponding to the determined initial sleep disordered breathing parameter is at or above a threshold; and determine an indication of low confidence if the received temperature information corresponding to the determined initial sleep disordered breathing parameter is below the threshold.

In Example 11, the subject matter of any one or more of Examples 1-10 may optionally be configured to include an implantable medical device comprising a temperature sensor configured to sense the temperature information and a respiration sensor configured to sense the temperature information of the patient.

In Example 12, the subject matter of any one or more of Examples 1-11 may optionally be configured such that the respiration sensor includes an impedance sensor configured to sense an impedance of the thorax of the patient and to determine respiration information of the patient using changes in the sensed impedance associated with patient respiration, the determined respiration information includes a determined tidal volume measure of the patient, and the assessment circuit is configured to determine the sleep disordered breathing parameter using a detected decrease in determined tidal volume measure of the patient from a baseline tidal volume measure over a detection window, the decrease greater than a sleep disordered breathing threshold.

In Example 13, the subject matter of any one or more of Examples 1-12 may optionally be configured such that the temperature sensor is configured to sense a temperature of a housing of the implantable cardiac monitor and to determine patient distal skin temperature using the sensed temperature information and the assessment circuit is configured to determine the sleep disordered breathing parameter using a combination of determined tidal volume measure of the patient over the detection window and the determined patient distal skin temperature corresponding to the detection window.

An example (e.g., "Example 14") of subject matter (e.g., a method) may comprise: receiving respiration information of a patient and temperature information of the patient using a signal receiver circuit; and determining, using an assessment circuit, a sleep disordered breathing parameter of the patient using a combination of the received respiration information and temperature information of the patient.

In Example 15, the subject matter of Example 14 may optionally be configured such that the respiration information comprises impedance information of the patient indicative of a tidal volume of the patient, the temperature information comprises a temperature of an implantable housing of the medical device system indicative of distal skin temperature of the patient, and determining the sleep disordered breathing parameter of the patient comprises using: (1) a detected decrease in the received impedance information from a baseline respiration measure over a detection window, the decrease greater than a sleep disordered breathing threshold, and (2) the temperature of the implantable housing corresponding to the detection window.

An example (e.g., "Example 16") of subject matter (e.g., an implantable cardiac monitor) may comprise: a respiration sensor configured to sense respiration information of a patient; a temperature sensor configured to sense temperature information of the patient; and an assessment circuit configured to determine a sleep disordered breathing parameter of the patient using the sensed respiration information of the patient and the sensed temperature information of the patient.

In Example 17, the subject matter of Example 16 may optionally be configured such that the respiration sensor includes an impedance sensor configured to sense an impedance of the thorax of the patient and to determine respiration information of the patient using changes in the sensed impedance associated with patient respiration, the determined respiration information includes a determined tidal volume measure of the patient, and the assessment circuit is configured to determine the sleep disordered breathing parameter using a detected decrease in determined tidal volume measure of the patient from a baseline tidal volume measure over a detection window, the decrease greater than a sleep disordered breathing threshold.

In Example 18, the subject matter of any one or more of Examples 1-17 may optionally be configured such that the temperature sensor is configured to sense a temperature of a housing of the implantable cardiac monitor and to determine patient distal skin temperature using the sensed temperature information and the assessment circuit is configured to determine the sleep disordered breathing parameter using a combination of determined tidal volume measure of the patient over the detection window and the determined patient distal skin temperature corresponding to the detection window.

In Example 19, the subject matter of any one or more of Examples 1-18 may optionally be configured such that the assessment circuit is configured to determine the sleep disordered breathing parameter using the detected decrease in the determined tidal volume measure of the patient greater than the sleep disordered breathing threshold and the determined patient distal skin temperature greater than a temperature threshold, the sleep disordered breathing parameter includes an indication that a sleep disordered breathing event has occurred over the detection window, and the assessment circuit is configured to determine the baseline tidal volume measure using the determined tidal volume measure of the patient over a baseline period longer than the detection window and preceding the detection window.

In Example 20, the subject matter of any one or more of Examples 1-19 may optionally be configured such that the detection window has a period between 5 and 15 seconds, and wherein the baseline period is a minute or longer.

In Example 21, the subject matter of any one or more of Examples 1-20 may optionally be configured such that the assessment circuit is configured to count a number of sleep disordered breathing events in a daily period and the assessment circuit is configured to adjust at least one of the sleep disordered breathing threshold or the length of the detection window using the sensed temperature information.

In Example 22, the subject matter of any one or more of Examples 1-21 may optionally be configured such that the assessment circuit is configured to determine the temperature threshold using a rate of change of the sensed temperature information.

In Example 23, the subject matter of any one or more of Examples 1-22 may optionally be configured such that the assessment circuit is configured to: determine an initial sleep disordered breathing parameter of the patient using the sensed respiration information and determine a confidence indication of the determined initial sleep disordered breathing parameter using the sensed temperature information.

In Example 24, the subject matter of any one or more of Examples 1-23 may optionally be configured such that the confidence indication includes indications of high confidence and low confidence and the assessment circuit is configured to: determine an indication of high confidence if the sensed temperature information corresponding to the determined initial sleep disordered breathing parameter is at or above a threshold; and determine an indication of low confidence if the sensed temperature information corresponding to the determined initial sleep disordered breathing parameter is below the threshold.

An example (e.g., "Example 25") of subject matter (e.g., a medical device system) may comprise: a signal receiver circuit configured to receive respiration information of a patient and temperature information of the patient; and an assessment circuit configured to determine a sleep disordered breathing parameter of the patient using the received respiration information and temperature information of the patient.

In Example 26, the subject matter of any one or more of Examples 1-25 may optionally be configured such that the respiration information comprises impedance information of the patient indicative of a tidal volume of the patient and the assessment circuit is configured to determine the sleep disordered breathing parameter using a detected decrease in the received impedance information from a baseline respiration measure over a detection window, the decrease greater than a sleep disordered breathing threshold.

In Example 27, the subject matter of any one or more of Examples 1-26 may optionally be configured such that the temperature information comprises a temperature of an implantable housing of the medical device system indicative of distal skin temperature of the patient and the assessment circuit is configured to determine the sleep disordered breathing parameter using a combination of the received impedance information over the detection window and the temperature of the implantable housing corresponding to the detection window.

In Example 28, the subject matter of any one or more of Examples 1-27 may optionally be configured such that the assessment circuit is configured to determine the sleep disordered breathing parameter using the detected decrease in the received impedance information indicative of the tidal volume of the patient greater than the sleep disordered breathing threshold and the temperature of the implantable housing greater than a temperature threshold, the sleep disordered breathing parameter includes an indication that a sleep disordered breathing event has occurred over the detection window, and the assessment circuit is configured to determine the baseline tidal volume measure using the determined tidal volume measure of the patient over a baseline period longer than the detection window and preceding the detection window.

In Example 29, the subject matter of any one or more of Examples 1-28 may optionally be configured such that the detection window has a period between 5 and 15 seconds, the baseline period is a minute or longer, the assessment circuit is configured to count a number of sleep disordered breathing events in a daily period, and the assessment circuit is configured to adjust at least one of the sleep disordered breathing threshold or the length of the detection window using the received temperature information.

In Example 30, the subject matter of any one or more of Examples 1-29 may optionally be configured such that the assessment circuit is configured to: determine an initial sleep disordered breathing parameter of the patient using the received respiration information and determine a confidence indication of the determined initial sleep disordered breathing parameter using the received temperature information.

In Example 31, the subject matter of any one or more of Examples 1-30 may optionally be configured such that the confidence indication includes indications of high confidence and low confidence and the assessment circuit is configured to: determine an indication of high confidence if the received temperature information corresponding to the determined initial sleep disordered breathing parameter is at or above a threshold and determine an indication of low confidence if the received temperature information corresponding to the determined initial sleep disordered breathing parameter is below the threshold.

An example (e.g., "Example 32") of subject matter (e.g., a method) may comprise: receiving respiration information of a patient and temperature information of the patient using a signal receiver circuit and determining, using an assessment circuit, a sleep disordered breathing parameter of the patient using a combination of the received respiration information and temperature information of the patient.

In Example 33, the subject matter of any one or more of Examples 1-32 may optionally be configured such that the respiration information comprises impedance information of the patient indicative of a tidal volume of the patient, the temperature information comprises a temperature of an implantable housing of the medical device system indicative of distal skin temperature of the patient, and determining the sleep disordered breathing parameter of the patient comprises using: (1) a detected decrease in the received impedance information from a baseline respiration measure over a detection window, the decrease greater than a sleep disordered breathing threshold, and (2) the temperature of the implantable housing corresponding to the detection window.

In Example 34, the subject matter of any one or more of Examples 1-33 may optionally be configured such that determining the sleep disordered breathing parameter includes determining an indication that a sleep disordered breathing event has occurred over the detection window, the method comprises determining the baseline respiration measure using the respiration information of the patient over a baseline period longer than and preceding the detection window, counting a number of sleep disordered breathing events of the patient in a daily period, and adjusting at least one of the sleep disordered breathing threshold or the length of the detection window using the received temperature information, wherein the detection window has a period between 5 and 15 seconds and the baseline period is a minute or longer.

In Example 35, the subject matter of any one or more of Examples 1-34 may optionally be configured such that determining the sleep disordered breathing parameter comprises: determine an initial sleep disordered breathing parameter of the patient using the received respiration information; and determine a confidence indication of the determined initial sleep disordered breathing parameter using the received temperature information.

In Example 36, subject matter (e.g., a system or apparatus) may optionally combine any portion or combination of any portion of any one or more of Examples 1-35 to comprise "means for" performing any portion of any one or more of the functions or methods of Examples 1-35, or at least one "non-transitory machine-readable medium" including instructions that, when performed by a machine, cause the machine to perform any portion of any one or more of the functions or methods of Examples 1-35.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
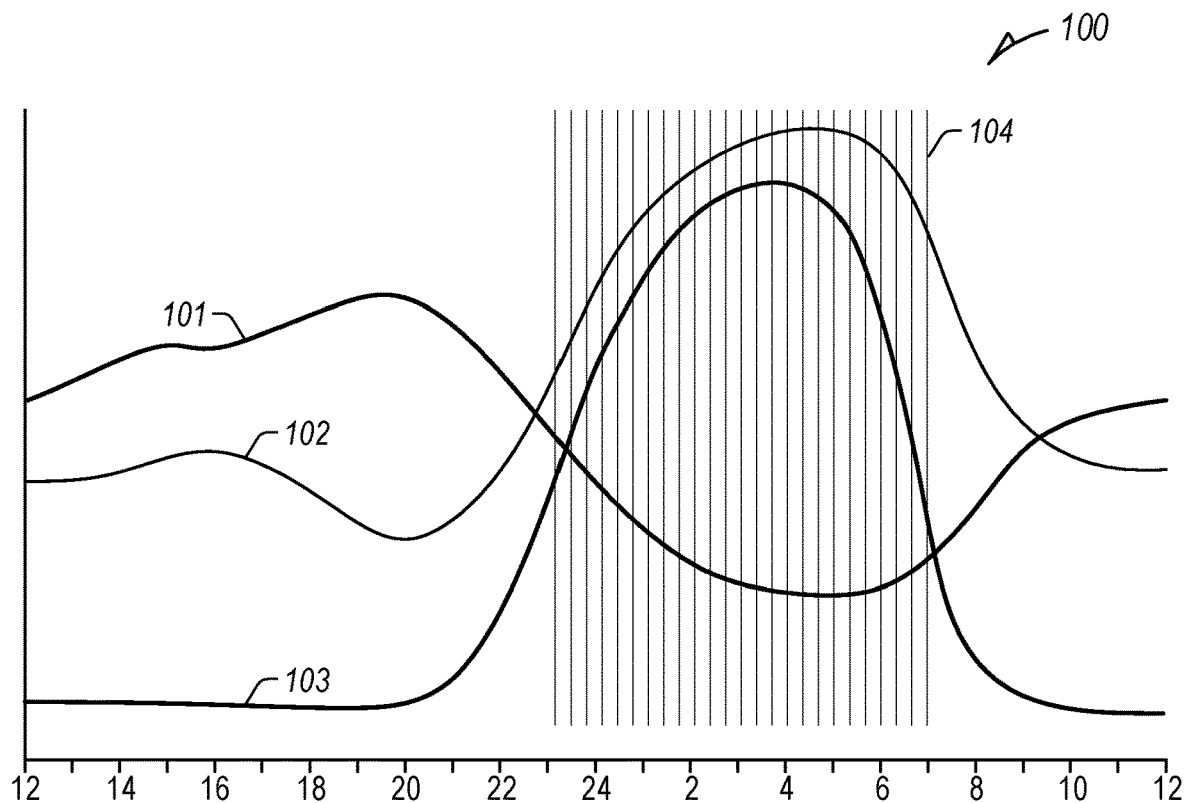
FIGS. 1 and 2 illustrate example relationships between patient circadian system aspects.

Sleep disordered breathing (SDB) is associated with a number of diseases that significantly impact morbidity and mortality. Sudden changes in oxygen flow associated with sleep apnea may provide additional strain on the heart and nervous system. Obstructed sleep apnea (OSA) is clinically associated with arterial hypertension, can increase risks of arrhythmia and stroke, and is highly prevalent in patients with type 2 diabetes. SDB is an indicator of coronary artery disease and associated with negative patient outcomes. Heart failure (HF) patients with SDB have a worse prognosis and increased mortality. There is also a large amount of overlap between patients with SDB, HF, and atrial fibrillation (AF).

Diagnosis of SDB relies heavily on accurate respiration sensing. Example scan algorithms for detecting SDB, such as apnea, look for periods of time (e.g., 10 seconds or greater, etc.) with a reduction in a baseline tidal volume (TV) above certain thresholds. For example, an AP scan algorithm can detect apnea/hypopnea events as a period of time, 10 seconds or greater, with an TV reduction greater than 26% (e.g., TV threshold of 0.74, etc.). Other systems may further distinguish between apneas and hypopneas, and/or monitor snoring or other obstructions or sleep disturbances to aid in SDB diagnosis. In other examples, one or more other periods (e.g., 5 to 15 seconds, etc.) or thresholds can be used, or in certain examples, combined with other physiologic information. For example, respiration information can be combined with patient activity information to detect SDB, such as described in the commonly assigned Lee et al. U.S. Pat. No. 7,469,697, titled "Feedback System and Method for Sleep Disordered Breathing Therapy", herein incorporated by reference in its entirety.

Once a cessation of breathing is identified, stimulation can be delivered to disrupt the episode, such as stimulation to the brain or one or more neural pathways, to the musculature of the airway, etc., to return the patient to normal respiration, or one or more other notifications can be provided to the patient or a clinician or other caregiver associated with the patient.

Ambulatory medical devices (AMDs) can be divided into two distinct groups: (1) external or wearable medical devices; and (2) implantable medical devices (IMDs), such as implantable (or insertable) cardiac monitors (ICMs), etc. The distinctions can be significant in power consumption, storage, communication, and patient compliance. Implantable medical devices have access to different physiological information, require different levels of signal and noise processing, and require little or no patient compliance (they cannot be forgotten), but cannot be replaced or recharged as easily as external or wearable medical devices. Further, communication inside and out of the body can be more challenging than equivalent communication outside the body. When detecting brief, intermittent episodes of physiologic information throughout the day, it is important to provide constant monitoring. For example, SDB episodes can be as little as a few seconds, with typical detection windows in the range of 10 seconds, out of 86,400 seconds in a day. In addition, it can be important to detect SDB episodes during time periods or in locations not commonly associated with nighttime sleep, such as naps during the day, during travel, etc. Accordingly, there are distinct differences between implantable and external medical devices.

AMDs, including ICMs (e.g., pacemakers, implantable cardiac defibrillators (ICDs), etc.), can include respiration sensors, such as impedance sensors configured to sense patient respiration for TV or minute volume (MV) measurements, for example, using changes in impedance measurements, etc. However, ambulatory respiration sensing can be challenging, as artifacts associated with patient motion, body position changes, or other interference can impact the accuracy of ambulatory respiration sensing. For example, a certain number of reductions in TV detected using an ICM are due to artifacts (e.g., motion artifacts, etc.) and not a reduction in breathing. Accordingly, the present inventors have recognized, among other things, a need to more reliably and accurately detect patient respiration information in AMDs, such as ICMs, etc., with respect to SDB events.

The present inventors have recognized that SDB significantly impairs the natural sleep-wake pattern and circadian system function. Unstable, fragmented sleep reduces stability of the natural temperature rhythm. SDB patients typically exhibit a higher daytime (awake) distal skin temperatures (DST) and lower nighttime (asleep) DST than healthy patients. Patient DST is generally associated with implant locations for traditional IMD or ICM housings (e.g., subcutaneous in an upper chest location of the patient, typically below the collar bone). Changes in patient core body temperature (CBT), the temperature of patient internal organs, such as the heart, etc., are typically inverse to changes in patient DST. As used herein, daytime and nighttime are used to refer to patient awake and sleep periods, respectively, and not necessarily to predetermined times of day (e.g., 10 pm to 8 am, etc.).

AMDs can include temperature sensors, such as thermistor or resistance-based temperature sensors, thermocouples, or one or more other electrical circuits configured to measure temperature information of the AMD or a patient associated with the AMD. In certain examples, the temperature sensor of an ICM or other IMD can be located inside a hermetically-sealed housing of the implantable device, isolated from or in direct contact with the housing, or in other examples, located outside the housing and having components in direct or close contact with body tissue. ICM temperature sensors can be precise, measuring temperature, such as at the site of implant (e.g., subcutaneous, etc.), with a precision up to 0.1° F., etc. Depending on implant site, ICM temperature may reflect patient skin temperature when located at or near the outer surface of the patient, such as implanted subcutaneously in the chest of patient, etc.

The present inventors have further recognized that monitoring circadian rhythm using measurements of patient temperature, such as patient DST, can be used to increase the accuracy of ambulatory respiration sensing with respect to SDB detection using AMDs, such as single-device ICM systems. As many ICM systems include a temperature sensor, combining measurements of patient temperature, such as patient DST measurements using a temperature sensor located on or within the ICM, with existing ICM respiration sensing can increase the accuracy of existing SDB detection, improving existing device performance without additional sensors or data sources.

In certain examples, the ICM, using one or more control or analysis circuits, can be configured to estimate a patient sleep status using measured ICM temperature. In certain examples, a high ICM temperature, relative to a patient daily temperature variation, can indicate that the patient is asleep, whereas a low ICM temperature, relative to the patient daily temperature variation, can indicate that the patient is awake. Further, ICM temperature measures can be used to indicate the quality of patient sleep or patient health status. This determination of patient sleep state, quality, or patient health status based on ICM temperature measures can be sued to improve the confidence of detected respiration variations (reductions in TV), such as to avoid false detections of SDB while the patient is awake, etc.

Accurate sleep detection using patient temperature information in a medical system can significantly improve SDB detection performance. In one example, traditional SDB detection using respiration information (e.g., a TV threshold of 0.74 over 10 seconds) provides a positive predictive value (PPV) and negative predictive value (NPV) of 0.882 and 0.769, respectively, whereas the addition of sleep detection using patient temperature information can increase the PPV and the NPV to 0.941 and 0.846, respectively, a significant improvement.

Figure 2:
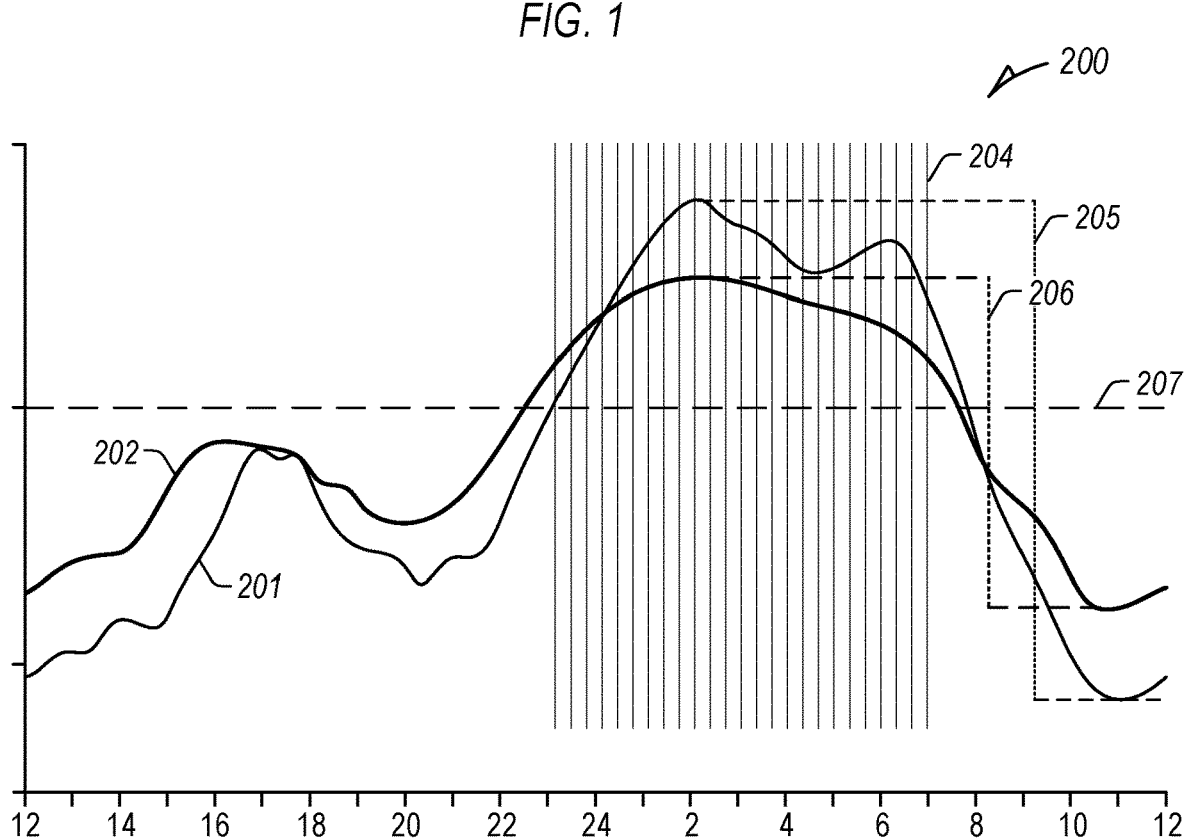

FIGS. 1 and 2 illustrate example relationships 100, 200 between patient circadian system aspects. FIG. 1 illustrates an example relationship 100 between patient circadian system aspects for a single daily period (12 pm to 12 pm) including relative changes in patient core body temperature (CBT) 101, sleep propensity 102, and melatonin level 103, illustrated with respect to a patient sleep period 104. FIG. 2 illustrates an example relationship 200 between healthy patient distal skin temperatures (DST) 201 and SDB patient DST 202 for a single daily period (12 pm to 12 pm) with respect to a patient sleep period 204.

Patient thermoregulation and sleep-wake cycle are strongly related. Patient CBT 101 decreases before and during the patient sleep period 104, whereas healthy patient DST 201 and SDB patient DST 202 increase before and during the patient sleep period 204. The beginning of the patient sleep period 104, 204 tends to coincide with the maximal decreasing rate of patient CBT 101, increase in melatonin level 103, and increase in healthy patient DST 201 and SDB patient DST 202. Sleep is difficult when distal skin areas (e.g., hands, feet, etc.) are cold. Warming distal skin areas promotes heat loss at the core and corresponding rapid sleep onset.

FIG. 2 illustrates absolute daily changes (deltas) in healthy patient DST 201 as a healthy DST variation 205 and in SDB patient DST 202 as an SDB DST variation 206. The healthy DST variation 205 is typically more pronounced (greater) than the SDB DST variation 206. The healthy patient 201 typically exhibits a lower daytime (awake) DST and higher nighttime (asleep) DST, with greater rates of increase and decrease at transitions between asleep and awake periods and throughout the day. In certain examples, measures of patient DST, such as changes in absolute daily changes or rates of change of increases and decreases in daily patient DST, daily maximum temperature, daily minimum temperature, inter-daily temperature variability, intra-daily temperature variability, sleep time versus wake time, etc., can be used to determine indications of SDB.

In certain examples, healthy patient DST 201 and SDB patient DST 202 above a temperature threshold 207 can indicate a patient sleep period 204. The temperature threshold 207 can be determined using temperature information of the patient. In an example, the temperature threshold 207 can be set to a temperature at a preset level (e.g., percentage) with respect to a preceding daily temperature range, a measure of one or more preceding days, etc. In other examples, the temperature threshold 207 can be set using a rate of change of temperature information alone, or after a specific time of day, or based on clinician input or other parameters.

More than just determining whether or not the patient is sleeping, changes in DST can provide an indication of sleep quality or patient health. Whereas activity information can provide indications of patient position and movement associated with whether or not the patient is in bed, variations in DST can indicate that the patient health status is improving or declining, independent of patient sleep time. As such, patient temperature information can provide clinically valuable information beyond that received from typical activity or position sensors. Trends of daily changes (increasing or decreasing) in one or more measures of patient DST can indicate changing patient status, vitality, disease progression or recovery, therapy or treatment efficacy, etc. One or more worsening measures of patient DST can be an early indication of arrhythmia, stroke, HF, worsening disease state, etc. As such, an indication or patient worsening using one or more measures of patient DST can trigger additional modes, sensing, notifications, or alerts.

Figure 3:
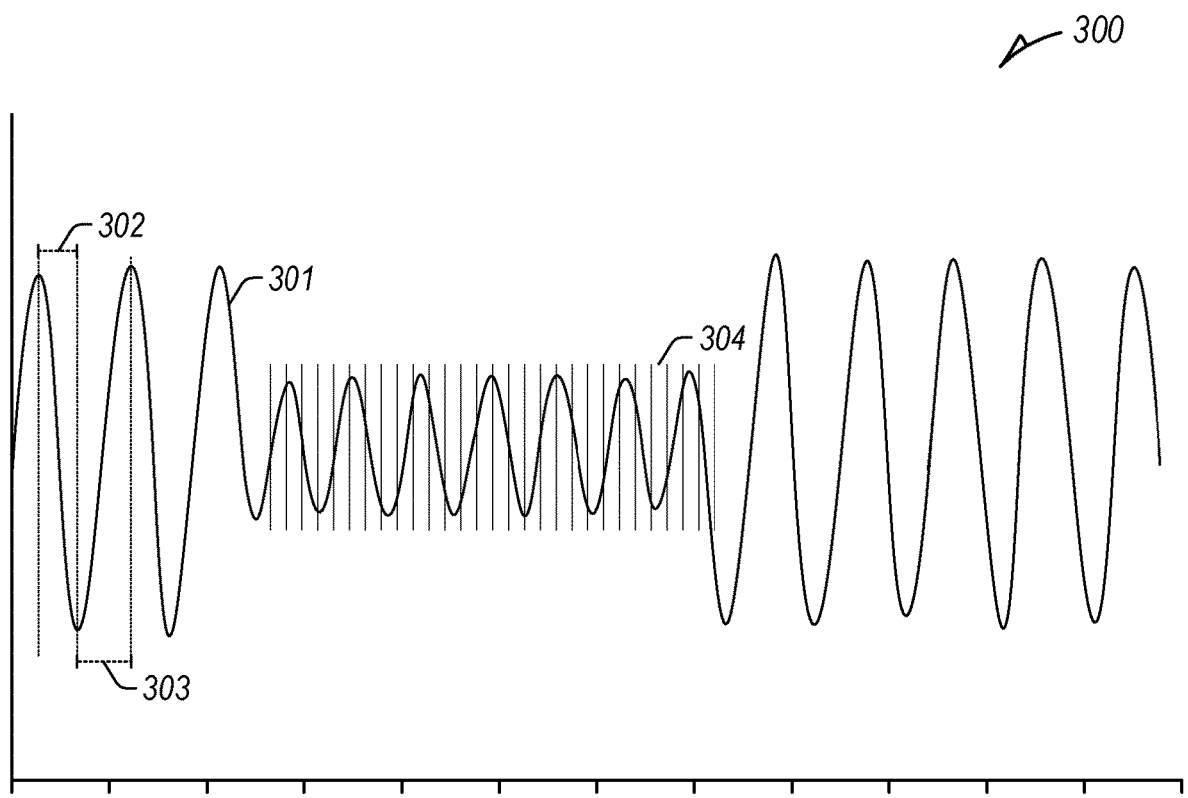
FIG. 3 illustrates example respiration information of a patient.

FIG. 3 illustrates example respiration information 300 of a patient including an impedance signal 301 proportional to the amount of air exhaled over an exhalation period 302 and inhaled over an inhalation period 303. The amount of air inhaled and exhaled over a respiration period is proportionate to a tidal volume (TV) of the patient. The impedance signal 301 illustrates a period of normal respiration with an intermittent sleep disordered breathing (SDB) episode 304 having a period of reduced TV greater than a detection window (e.g., 10 seconds).

Figure 4:
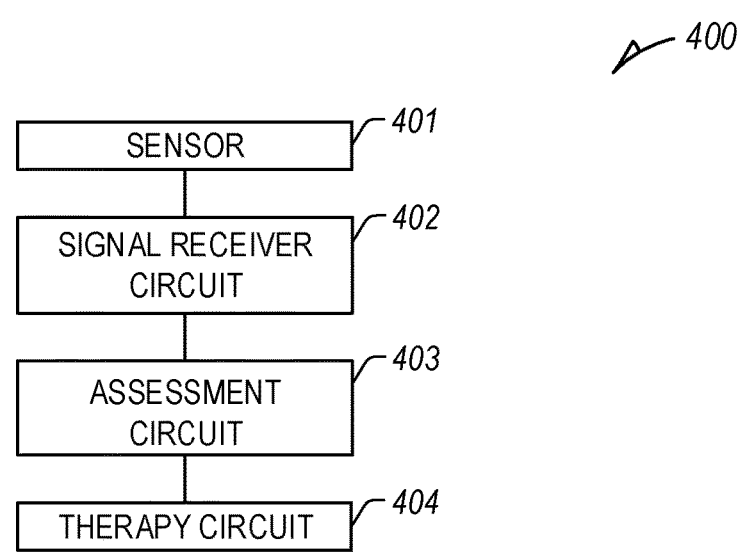
FIG. 4 illustrates an example system.

FIG. 4 illustrates an example system 400, such as a medical-device system, etc. In an example, one or more aspects of the example system 400 can be a component of, or communicatively coupled to, an ambulatory medical device (AMD), such as an implantable cardiac monitor (ICM), etc. AMDs can be configured to monitor, detect, or treat various physiologic conditions of the body, such as cardiac conditions associated with a reduced ability of a heart to sufficiently deliver blood to a body, including heart failure (HF), arrhythmias, hypertension, dyssynchrony, etc., or one or more other physiologic conditions, such as sleep disordered breathing (SDB), etc., and, in certain examples, can be configured to provide electrical stimulation or one or more other therapies or treatments to the patient.

The system 400 can include a single AMD or a plurality of AMDs implanted in a patient's body or otherwise positioned on or about the patient to monitor patient physiologic information of the patient using one or more sensors, such as a sensor 401. In an example, the sensor 401 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a temperature sensor; a skin elasticity sensor, or one or more other sensors configured to receive physiologic information of the patient.

The example system 400 can include a signal receiver circuit 402 and an assessment circuit 403. The signal receiver circuit 402 can be configured to receive physiologic information of a patient (or group of patients) from one or more sensors 401. The assessment circuit 403 can be configured to receive information from the signal receiver circuit 402, and to determine one or more parameters (e.g., physiologic parameters, stratifiers, etc.) or existing or changed patient conditions (e.g., indications of patient dehydration, respiratory condition, cardiac condition (e.g. HF, arrhythmia), SDB, etc.) using the received physiologic information, such as described herein. The physiologic information can include, among other things, cardiac electrical information, impedance information, respiration information, heart sound information, activity information, posture information, temperature information, chemical information, or one or more other types of physiologic information.

The assessment circuit 403 can be configured to provide an output to a user, such as to a display or one or more other user interface, the output including a score, a trend, an alert, or other indication. In other examples, the assessment circuit 403 can be configured to provide an output to another circuit, machine, or process, such as a therapy circuit 404 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more CRT parameters, drug delivery, dosage determinations or recommendations, etc. In an example, the therapy circuit 404 can include one or more of a stimulation control circuit, a cardiac stimulation circuit, a neural stimulation circuit, a dosage determination or control circuit, etc. In other examples, the therapy circuit 404 can be controlled by the assessment circuit 403, or one or more other circuits, etc.

AMDs can include a range of medical devices, including, for example, traditional cardiac rhythm management (CRM) devices, such as implantable cardiac monitors (ICMs), pacemakers, defibrillators, or cardiac resynchronizers, include implantable or subcutaneous devices having hermetically sealed housings configured to be implanted in a chest of a patient. The CRM device can include one or more leads to position one or more electrodes or other sensors at various locations in or near the heart, such as in one or more of the atria or ventricles. Accordingly, CRM devices can include aspects located subcutaneously, though proximate the distal skin of the patient, as well as aspects, such as leads or electrodes, located near one or more organs of the patient. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from the patient, or provide one or more therapies or stimulation to the patient.

Implantable devices can additionally or separately include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Each additional sensor within or associated with an AMD or medical device system can increase system cost and complexity, reduce system reliability, or increase the power consumption and reduce the usable life of the AMD. Accordingly, it can be beneficial to use a single sensor to determine multiple types of physiologic information, or a smaller number of sensors to measure a larger number of different types of physiologic information. For example, it can be beneficial to detect atrial cardiac electrical information without a lead or an electrode in, or in contact with, the atria. Similarly, it can be beneficial to detect accurate respiration phase information without a direct measurement of patient airflow.

Figure 5:
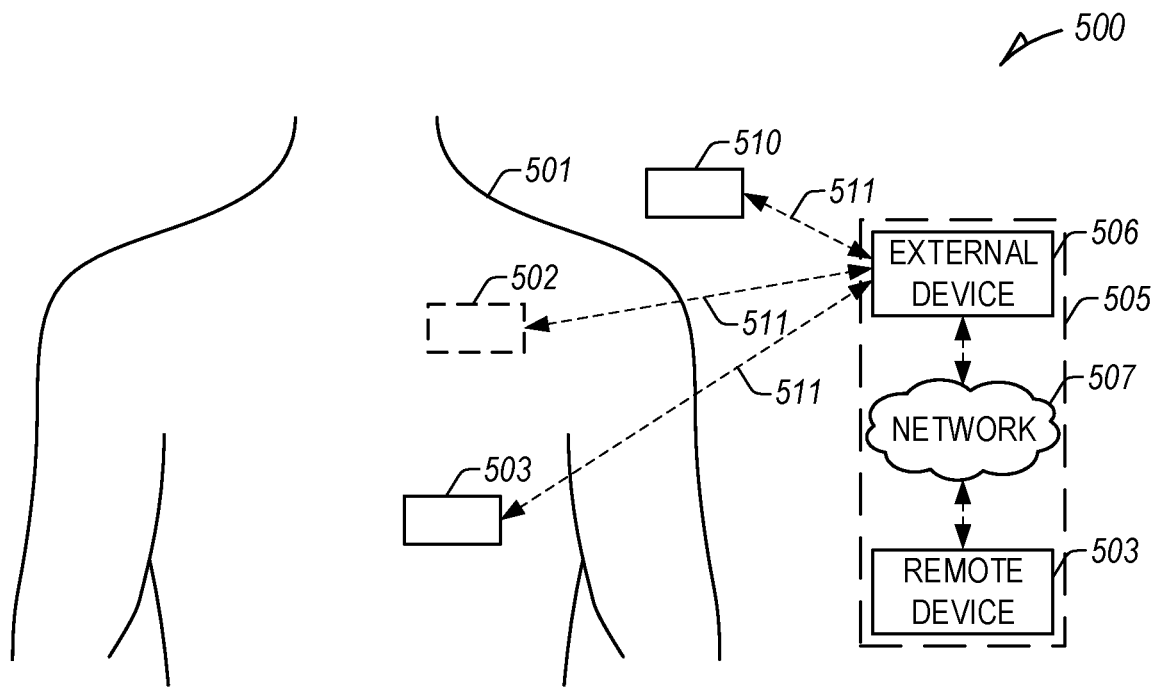
FIG. 5 illustrates an example patient management system.

FIG. 5 illustrates an example patient management system 500 and portions of an environment in which the system 500 may operate. The patient management system 500 can perform a range of activities, including remote patient monitoring and diagnosis of a disease condition. Such activities can be performed proximal to a patient 501, such as in a patient home or office, through a centralized server, such as in a hospital, clinic, or physician office, or through a remote workstation, such as a secure wireless mobile computing device.

The patient management system 500 can include one or more ambulatory medical devices (AMDs), an external system 505, and a communication link 511 providing for communication between the one or more AMDs and the external system 505. The one or more AMDs can include an implantable medical device (IMD) 502 (e.g., an implantable cardiac monitor (ICM), etc.), a wearable medical device 503, or one or more other implantable, leadless, subcutaneous, external, wearable, or AMDs configured to monitor, sense, or detect information from, determine physiologic information about, or provide one or more therapies to treat various conditions of the patient 501, such as one or more cardiac or non-cardiac conditions (e.g., dehydration, SDB, etc.).

In an example, the IMD 502 can include one or more traditional cardiac rhythm management (CRM) or implantable cardiac monitor (ICM) devices, such as a pacemaker or defibrillator, implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 501. In another example, the IMD 502 can include a monitor implanted, for example, subcutaneously in the chest of patient 501, the IMD 502 including a housing containing circuitry and, in certain examples, one or more sensors, such as a temperature sensor, etc.

The IMD 502 can include an assessment circuit configured to detect or determine specific physiologic information of the patient 501, or to determine one or more conditions or provide information or an alert to a user, such as the patient 501 (e.g., a patient), a clinician, or one or more other caregivers or processes. The IMD 502 can alternatively or additionally be configured as a therapeutic device configured to treat one or more medical conditions of the patient 501. The therapy can be delivered to the patient 501 via the lead system and associated electrodes or using one or more other delivery mechanisms. The therapy can include delivery of one or more drugs to the patient 501 using the IMD 502 or one or more of the other AMDs. In some examples, therapy can include CRT for rectifying dyssynchrony and improving cardiac function in CHF patients. In other examples, the IMD 502 can include a drug delivery system, such as a drug infusion pump to deliver drugs to the patient for managing arrhythmias or complications from arrhythmias, hypertension, or one or more other physiologic conditions. In other examples, the IMD 502 can include one or more electrodes configured to stimulate the nervous system of the patient or to provide stimulation to the muscles of the patient airway, etc.

The wearable medical device 503 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). The wearable medical device 503 can include an optical sensor configured to detect a PPG signal on a wrist, finger, or other location on the patient 501. In other examples, the wearable medical device 503 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The external system 505 can include a dedicated hardware/software system, such as a programmer, a remote server-based patient management system, or alternatively a system defined predominantly by software running on a standard personal computer. The external system 505 can manage the patient 501 through the IMD 502 or one or more other AMDs connected to the external system 505 via a communication link 511. In other examples, the IMD 502 can be connected to the wearable device 503, or the wearable device 503 can be connected to the external system 505, via the communication link 511. This can include, for example, programming the IMD 502 to perform one or more of acquiring physiologic data, performing at least one self-diagnostic test (such as for a device operational status), analyzing the physiologic data to detect a cardiac arrhythmia, or optionally delivering or adjusting a therapy to the patient 501. Additionally, the external system 505 can send information to, or receive information from, the IMD 502 or the wearable device 503 via the communication link 511. Examples of the information can include real-time or stored physiologic data from the patient 501, diagnostic data, such as detection of patient hydration status, hospitalizations, responses to therapies delivered to the patient 501, or device operational status of the IMD 502 or the wearable device 503 (e.g., battery status, lead impedance, etc.). The communication link 511 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 505 can include an external device 506 in proximity of the one or more AMDs, and a remote device 508 in a location relatively distant from the one or more AMDs, in communication with the external device 506 via a communication network 507. Examples of the external device 506 can include a medical device programmer.

The remote device 508 can be configured to evaluate collected patient or patient information and provide alert notifications, among other possible functions. In an example, the remote device 508 can include a centralized server acting as a central hub for collected data storage and analysis. The server can be configured as a uni-, multi-, or distributed computing and processing system. The remote device 508 can receive data from multiple patients. The data can be collected by the one or more AMDs, among other data acquisition sensors or devices associated with the patient 501. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more AMDs, such as the IMD. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 508 may additionally include one or more locally configured clients or remote clients securely connected over the communication network 507 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 508, including the server and the interconnected clients, may also execute a follow-up scheme by sending follow-up requests to the one or more AMDs, or by sending a message or other communication to the patient 501 (e.g., the patient), clinician or authorized third party as a compliance notification.

The communication network 507 can provide wired or wireless interconnectivity. In an example, the communication network 507 can be based on the Transmission Control Protocol/Internet Protocol (TCP/IP) network communication specification, although other types or combinations of networking implementations are possible. Similarly, other network topologies and arrangements are possible.

One or more of the external device 506 or the remote device 508 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 506 or the remote device 508 can include a respective display unit for displaying the physiologic or functional signals, or alerts, alarms, emergency calls, or other forms of warnings to signal the detection of arrhythmias. In some examples, the external system 505 can include an external data processor configured to analyze the physiologic or functional signals received by the one or more AMDs, and to confirm or reject the detection of arrhythmias. Computationally intensive algorithms, such as machine-learning algorithms, can be implemented in the external data processor to process the data retrospectively to detect cardia arrhythmias.

Portions of the one or more AMDs or the external system 505 can be implemented using hardware, software, firmware, or combinations thereof. Portions of the one or more AMDs or the external system 505 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 500 can include a therapy device 510, such as a respiratory therapy device (e.g. continuous positive airway pressure device or nebulizer device, etc.) or a drug delivery device configured to provide therapy or therapy information (e.g., dosage information, etc.) to the patient 501, such as using information from one or more of the AMDs. In other examples, one or more of the AMDs can be configured to provide therapy or therapy information to the patient 501. The therapy device 510 can be configured to send information to or receive information from one or more of the AMDs or the external system 505 using the communication link 511. In an example, the one or more AMDs, the external device 506, or the remote device 508 can be configured to control one or more parameters of the therapy device 510.

The external system 505 can allow for programming the one or more AMDs and can receives information about one or more signals acquired by the one or more AMDs, such as can be received via a communication link 511. The external system 505 can include a local external IMD programmer. The external system 505 can include a remote patient management system that can monitor patient status or adjust one or more therapies such as from a remote location.

The assessment circuit may be implemented at the external system 505, which can be configured to perform HF risk stratification such as using data extracted from the one or more AMDs or data stored in a memory within the external system 505. Portions of patient chronic condition-based HF or other assessment circuit may be distributed between the one or more AMDs and the external system 505.

Figure 6:
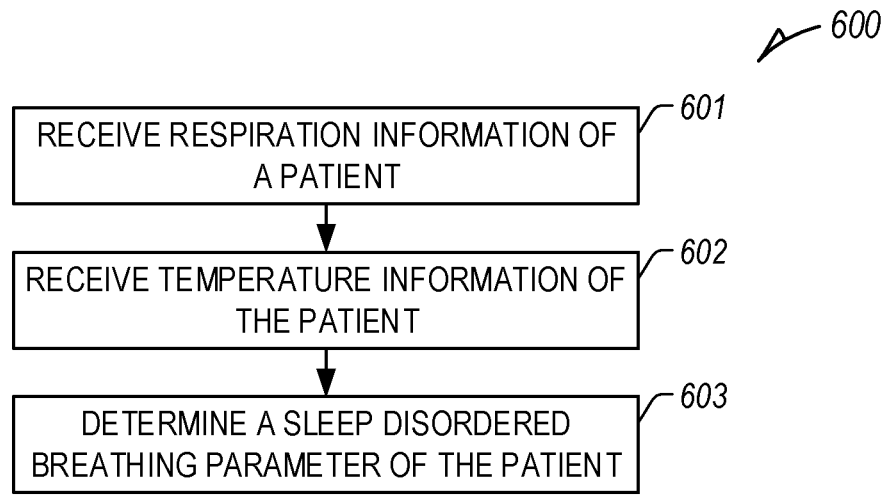
FIGS. 6 and 7 illustrate example methods of determining a sleep disordered breathing (SDB) parameter of a patient.
Figure 7:
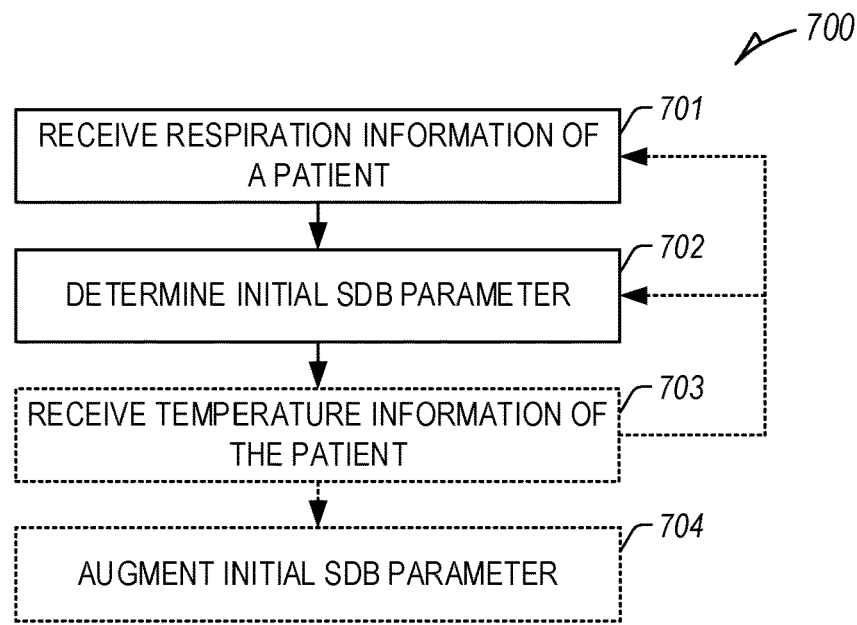

FIGS. 6 and 7 illustrate example methods 600, 700 of determining a sleep disordered breathing (SDB) parameter of a patient. At 601, respiration information of the patient can be received, such as a measure or indication of tidal volume (TV) from a respiration sensor (e.g., a thoracic impedance based respiration sensor, etc.). In certain examples, a patient respiration baseline can be determined using the received respiration information over a baseline period preceding a detection window. In an example, the baseline period can include a period of a minute or longer. In other examples, the baseline period can be longer. In certain examples, the patient respiration baseline can include a daily respiration baseline, a short-term respiration baseline of the past several days of the patient (e.g., 1 to 3 days, etc.), or long-term respiration baseline of the past several weeks (e.g., 1 to 3 weeks, etc.). In other examples, the patient respiration baseline can be determined specifically for detected or predetermined periods of wake or sleep (e.g., a short-term nighttime respiration baseline, etc.).

At 602, temperature information of the patient can be received, such as a measure of temperature from a temperature sensor. In certain examples, a patient temperature profile can be determined including one or more parameters indicative of patient thermoregulation throughout the day. The one or more parameters can include a daily temperature delta, a rate of temperature increase or decrease, or one or more parameters indicative of changes in daily temperature deltas or rates of temperature increase or decrease over time.

At 603, an SDB parameter of the patient can be determined, such as using an assessment circuit of one or more medical device components, such as an implantable cardiac monitor (ICM), etc. In certain examples, patient temperature information (e.g., ICM temperature) can be combined with or used to augment SDB detection using patient respiration information, such as to reduce false SDB detections or more accurately classify borderline SDB detections or provide confidence indications of SDB determinations. False positive SDB detections can occur during daytime or awake periods of reduced measures of respiration information (e.g., TV threshold of 0.74), such as due to noise, artifacts, etc. In certain examples, borderline SDB detections using respiration information (e.g., reductions in patient respiration at or near an SDB threshold) can be confirmed or rejected using patient temperature information. In an example, SDB detection can be gated using temperature information, such that SDB detection does not occur during periods of low ICM temperature or distal skin temperature. In other examples, one or more SDB thresholds can be adjusted using temperature information. For example, an SDB threshold can be adjusted during periods of low ICM temperature (e.g., TV of 0.70-0.74 or less).

In certain examples, the probability of a patient experiencing an SDB episode (p(SDB)) can be determined as a function of a probability of SDB determined using respiration information (p(SDB|TV)) (e.g., a reduction in TV over a period with respect to a baseline) and a probability of sleep state determined using temperature information (p(insleep|temp)) (e.g., ICM temperature information for the period with respect to thermoregulation cycle) adjusted by one or more coefficients (e.g., A).

$$p(\text{SDB})=p(\text{SDB}|\text{TV}) \times A(p(\text{insleep}|\text{temp})) \quad (1)$$

In an example, an SDB event can be detected when p(SDB) exceeds a threshold. In certain examples, the number of SDB events can be counted or determined, such as for a sleep period, or a determination of sleep quality can be determined using the number of periods (e.g., 10 second periods) having a p(SDB) above a threshold, such as using an assessment circuit. In certain examples, one or more detected SDB episodes can be used to trigger additional patient monitoring, change modes in one or more implantable or ambulatory medical devices associated with the patient, such as increasing the number or resolution of physiologic sensors, increasing resolution or periods of storage of physiologic information, triggering patient feedback, etc. In certain examples, if no indications of SDB are determined, the one or more medical devices can reduce one or more sampling or storage parameters to reduce power consumption and increase device battery lifespan.

FIG. 7 illustrates an example method 700 of augmenting a determined initial sleep disordered breathing (SDB) parameter of a patient. At 701, respiration information of the patient can be received. At 702, an initial SDB parameter of the patient can be determined, such as using an assessment circuit of one or more medical device components and the received respiration information. At 703, temperature information of the patient can be received, such as a measure of temperature from a temperature sensor associated with patient distal skin temperature (DST). At 704, the initial SDB parameter can be augmented using the received temperature information.

In other examples, the received temperature information can be used to adjust respiration sensing of the patient, such as gating the respiration information received for SDB detection or increasing or decreasing sampling rate or the type of respiration information detected to reduce power consumption for SDB detection during times of low patient DST or normal DST variation. For example, in certain examples, respiration rate can be detected using lower power consumption than tidal volume measurements. As such, temperature information can be used to switch between, or turn on and off, certain respiration sensing, such as to save power or avoid false positives. In addition, the frequency of detection or sampling rates can be adjusted to detect higher resolution respiration information or more frequently detect respiration information based on received temperature information, such as to save power during periods of low DST where a patient is unlikely to be asleep, etc.

In an example, the initial SDB parameter can include a traditional SDB parameter determined using respiration information. The initial SDB parameter can be augmented, such as using patient temperature information to provide a confidence indication of the initial SDB parameter or one or more SDB detections based on respiration information. For example, a reduction in TV above a threshold with a high ICM temperature can be indicated as a high confidence SDB or apnea event, whereas a reduction in TV above the threshold with a low ICM temperature can be indicated as a low confidence SDB or apnea event.

In certain examples, SDB can disturb thermal regulation. Accordingly, in certain examples, temperature information alone, or changes in temperature information, can be used to determine indications of SDB. For example, deviations from a patient long-term baseline can indicate a change in patient status. A decrease in the change in daily patient temperature can indicate a higher likelihood of SDB or a negative change in patient status or sleep state. In other examples, a probabilistic measure of SDB (p(SDB)) can be determined using a combination of respiration information and temperature information in both sleep and out of sleep periods, where sleep periods and out of sleep periods are determined using temperature information:

$$p(\text{SDB})=p(\text{SDB}|\text{insleep}) \times p(\text{insleep})+p(\text{SDB}|\text{out of sleep})(1-p(\text{insleep})) \quad (2)$$

In other examples, temperature information, or changes in temperature information, can be used to adjust one or more other SDB metrics, such as TV thresholds, time windows associated with TV thresholds (e.g., 10 second windows can be decreased by one or more seconds if received temperature information indicates that the patient is asleep, increased by one or more seconds if received temperature information indicates that the patient is awake, etc.), etc. In other examples, instead of or in addition to TV thresholds, one or more other respiration measurements (e.g., mid-term baseline (MTBL) of minute ventilation (MV) information, etc.) can be used.

Figure 8:
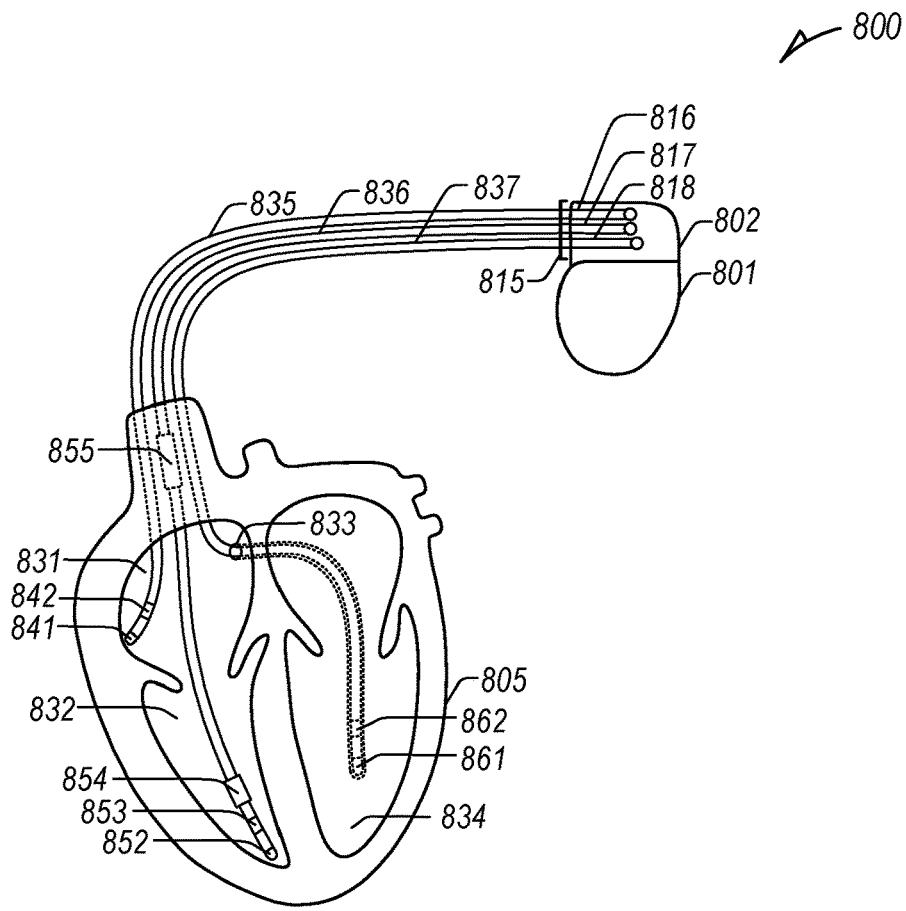
FIG. 8 illustrates an example implantable medical device (IMD).

FIG. 8 illustrates an example IMD 800 electrically coupled to a heart 805 such as through one or more leads, such as first, second, or third leads 835, 836, 837 coupled to the IMD 800 through lead ports 815, such as first, second, or third lead ports 816, 817, 818 in a header 802 of the IMD 800. In an example, the IMD 800 can include an antenna, such as in the header 802, configured to enable communication with an external system (such as an external system 605 illustrated in FIG. 6).

The IMD 800 may include an implantable medical device (IMD), such as an implantable cardiac monitor (ICM), pacemaker, defibrillator, cardiac resynchronizer, or other subcutaneous IMD configured to be implanted in a chest of a subject, having one or more leads to position one or more electrodes or other sensors at various locations in or near the heart 805, such as in one or more of the atria or ventricles. Separate from, or in addition to, the one or more electrodes or other sensors of the leads, the IMD 800 can include one or more electrodes or other sensors (e.g., a pressure sensor, an accelerometer, a gyroscope, a microphone, etc.) powered by a power source in the IMD 800. The one or more electrodes or other sensors of the leads, the IMD 800, or a combination thereof, can be configured detect physiologic information from, or provide one or more therapies or stimulation to, the patient.

Implantable devices can additionally include leadless cardiac pacemakers (LCP), small (e.g., smaller than traditional implantable devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart 805 without traditional lead or implantable device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

The IMD 800 can include one or more monitoring or therapeutic devices such as a subcutaneously implanted device, a wearable external device, a neural stimulator, a drug delivery device, a biological therapy device, or one or more other ambulatory medical devices. The IMD 800 may be coupled to, or may be substituted by a monitoring medical device such as a bedside or other external monitor.

The IMD 800 can include a hermetically sealed housing (CAN) 801 that can house an electronic circuit that can sense a physiologic signal in the heart 805 and can deliver one or more therapeutic electrical pulses to a target region, such as in the heart, such as through one or more leads (e.g., the first, second, and third leads 835, 836, 837). In certain examples, the CRM system 800 can include only a single lead, such as the second lead 836, or can include only two leads, such as the first and second leads 835, 836.

The first lead 835 can include a proximal end that can be configured to be connected to IMD 800 and a distal end that can be configured to be placed at a target location such as in the right atrium (RA) 831 of the heart 805. The first lead 835 can have a first pacing-sensing electrode 841 that can be located at or near its distal end, and a second pacing-sensing electrode 842 that can be located at or near the electrode 841. The first and second pacing-sensing electrodes 841, 842 can be electrically connected to the IMD 800 such as via separate conductors in the first lead 835, such as to allow for sensing of the right atrial activity and optional delivery of atrial pacing pulses. The second lead 836 can be a defibrillation lead that can include a proximal end that can be connected to IMD 800 and a distal end that can be placed at a target location such as in the right ventricle (RV) 832 of heart 805. The second lead 836 can have a first pacing-sensing electrode 852 that can be located at distal end, a second pacing-sensing electrode 853 that can be located near the first pacing-sensing electrode 852, a first defibrillation coil electrode 854 that can be located near the second pacing-sensing electrode 853, and a second defibrillation coil electrode 855 that can be located at a distance from the distal end such as for superior vena cava (SVC) placement. The first, second, and third pacing-sensing electrodes 852-855 can be electrically connected to the IMD 800 such as via separate conductors in the second lead 836. The first and second pacing-sensing electrodes 852, 853 can allow for sensing of a ventricular electrogram and can optionally allow delivery of one or more ventricular pacing pulses, and the first and second defibrillation coil electrodes 854, 855 can allow for delivery of one or more ventricular cardioversion/defibrillation pulses. In an example, the second lead 836 can include only three electrodes, first, second, and third electrodes 852, 854, 855. The first and second electrodes 852, 854 can be used for sensing or delivery of one or more ventricular pacing pulses, and the second and third electrodes 854, 855 can be used for delivery of one or more ventricular cardioversion or defibrillation pulses. The third lead 837 can include a proximal end that can be connected to the IMD 800 and a distal end that can be configured to be placed at a target location such as in a left ventricle (LV) 834 of the heart 805. The third lead 837 may be implanted through the coronary sinus 833 and may be placed in a coronary vein over the LV such as to allow for delivery of one or more pacing pulses to the LV. The third lead 837 can include a first electrode 861 that can be located at a distal end of the third lead 837 and a second electrode 862 that can be located near the first electrode 861. The first and second electrodes 861, 862 can be electrically connected to the IMD 800 such as via separate conductors in the third lead 837 such as to allow for sensing of the LV electrogram and optionally allow delivery of one or more resynchronization pacing pulses from the LV.

The IMD 800 can include an electronic circuit that can sense a physiologic signal. The physiologic signal can include an electrogram or a signal representing mechanical function of the heart 805. The CAN 801 may function as an electrode such as for sensing or pulse delivery. For example, an electrode from one or more of the leads may be used together with the CAN 801 such as for unipolar sensing of an electrogram or for delivering one or more pacing pulses. A defibrillation electrode from the second lead 836 may be used together with the CAN 801 such as for delivering one or more cardioversion/defibrillation pulses. In an example, the IMD 800 can sense impedance such as between electrodes located on one or more of the leads or the CAN 801. The IMD 800 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 800 can be configured to inject current between an electrode on the second lead 836 and the CAN 801, and to sense the resultant voltage between the same electrodes or between a different electrode on the second lead 836 and the CAN 801. A physiologic signal can be sensed from one or more physiologic sensors that can be integrated within the IMD 800. The IMD 800 can also be configured to sense a physiologic signal from one or more external physiologic sensors or one or more external electrodes that can be coupled to the IMD 800. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

An external system can allow for programming of the IMD 800 and can receives information about one or more signals acquired by IMD 800, such as received via a communication link using an antenna and a telemetry circuit. The external system can include a local external IMD programmer. The external system can include a remote patient management system that can monitor patient status or adjust one or more therapies such as from a remote location.

The communication link can provide for data transmission between the IMD 800 and the external system. The transmitted data can include, for example, real-time physiologic data acquired by the IMD 800, physiologic data acquired by and stored in the IMD 800, therapy history data or data indicating IMD operational status stored in the IMD 800, one or more programming instructions to the IMD 800 such as to configure the IMD 800 to perform one or more actions that can include physiologic data acquisition such as using programmably specifiable sensing electrodes and configuration, device self-diagnostic test, or delivery of one or more therapies.

Portions of the IMD 800 or the external system can be implemented using hardware, software, or any combination of hardware and software. Portions of the IMD 800 or the external system may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 800, the CRM system 800 can include a subcutaneous medical device (e.g., subcutaneous ICD, subcutaneous diagnostic device), wearable medical devices (e.g., patch-based sensing device), or other external medical devices.

Figure 9:
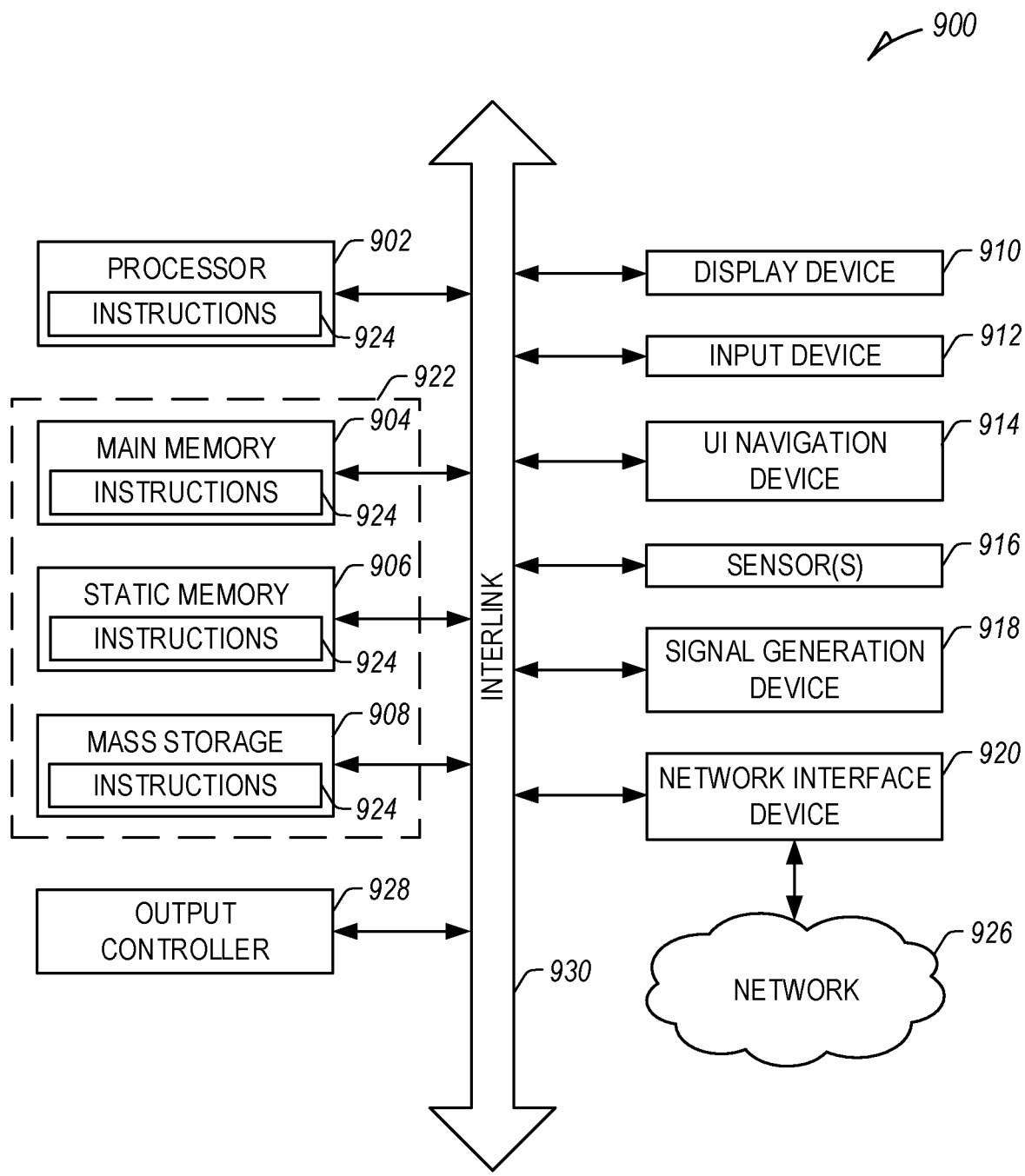
FIG. 9 illustrates a block diagram of an example machine upon which any one or more of the techniques (e.g., methodologies) discussed herein may perform.

FIG. 9 illustrates a block diagram of an example machine 900 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 900. Circuitry (e.g., processing circuitry, an assessment circuit, etc.) is a collection of circuits implemented in tangible entities of the machine 900 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 900 follow.

In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 900 may include a hardware processor 902 (e.g., a central processing unit (CPU), a graphics processing unit (GPU), a hardware processor core, or any combination thereof), a main memory 904, a static memory (e.g., memory or storage for firmware, microcode, a basic-input-output (BIOS), unified extensible firmware interface (UEFI), etc.) 906, and mass storage 908 (e.g., hard drive, tape drive, flash storage, or other block devices) some or all of which may communicate with each other via an interlink (e.g., bus) 930. The machine 900 may further include a display unit 910, an alphanumeric input device 912 (e.g., a keyboard), and a user interface (UI) navigation device 914 (e.g., a mouse). In an example, the display unit 910, input device 912, and UI navigation device 914 may be a touch screen display. The machine 900 may additionally include a signal generation device 918 (e.g., a speaker), a network interface device 920, and one or more sensors 916, such as a global positioning system (GPS) sensor, compass, accelerometer, or one or more other sensors. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 902, the main memory 904, the static memory 906, or the mass storage 908 may be, or include, a machine-readable medium 922 on which is stored one or more sets of data structures or instructions 924 (e.g., software) embodying or utilized by any one or more of the techniques or functions described herein. The instructions 924 may also reside, completely or at least partially, within any of registers of the processor 902, the main memory 904, the static memory 906, or the mass storage 908 during execution thereof by the machine 900. In an example, one or any combination of the hardware processor 902, the main memory 904, the static memory 906, or the mass storage 908 may constitute the machine-readable medium 922. While the machine-readable medium 922 is illustrated as a single medium, the term "machine-readable medium" may include a single medium or multiple media (e.g., a centralized or distributed database, and/or associated caches and servers) configured to store the one or more instructions 924.

The term "machine-readable medium" may include any medium that is capable of storing, encoding, or carrying instructions for execution by the machine 900 and that cause the machine 900 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 924 may be further transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 900, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. An implantable cardiac monitor, comprising:
   a respiration sensor configured to sense respiration information of a patient;
   a temperature sensor configured to sense temperature information of a housing of the implantable cardiac monitor; and
   an assessment circuit configured to determine distal skin temperature of the patient using the sensed temperature information and to determine a sleep disordered breathing parameter of the patient using the sensed respiration information of the patient and the determined distal skin temperature of the patient.

2. The implantable cardiac monitor of claim 1, wherein the respiration sensor includes an impedance sensor configured to sense an impedance of the thorax of the patient and to determine respiration information of the patient using changes in the sensed impedance associated with patient respiration,
   wherein the determined respiration information includes a determined tidal volume measure of the patient, and
   wherein the assessment circuit is configured to determine the sleep disordered breathing parameter using a detected decrease in the determined tidal volume measure of the patient greater than a sleep disordered breathing threshold from a baseline tidal volume measure over a detection window.

3. The implantable cardiac monitor of claim 2, wherein the assessment circuit is configured to determine the sleep disordered breathing parameter using a combination of determined tidal volume measure of the patient over the detection window and the determined patient distal skin temperature corresponding to the detection window.

4. The implantable cardiac monitor of claim 3, wherein the assessment circuit is configured to determine the sleep disordered breathing parameter using the detected decrease in the determined tidal volume measure of the patient greater than the sleep disordered breathing threshold and the determined patient distal skin temperature greater than a temperature threshold,
- wherein the sleep disordered breathing parameter includes an indication that a sleep disordered breathing event has occurred over the detection window, and
- wherein the assessment circuit is configured to determine the baseline tidal volume measure using the determined tidal volume measure of the patient over a baseline period longer than the detection window and preceding the detection window.

5. The implantable cardiac monitor of claim 4, wherein the detection window has a period between 5 and 15 seconds, and wherein the baseline period is a minute or longer.

6. The implantable cardiac monitor of claim 4, wherein the assessment circuit is configured to count a number of sleep disordered breathing events in a daily period, and
- wherein the assessment circuit is configured to adjust at least one of the sleep disordered breathing threshold or the length of the detection window using the sensed temperature information.

7. The implantable cardiac monitor of claim 3, wherein the assessment circuit is configured to determine the temperature threshold using a rate of change of the sensed temperature information.

8. The implantable cardiac monitor of claim 2, wherein the assessment circuit is configured to:
- determine an initial sleep disordered breathing parameter of the patient using the sensed respiration information; and
- determine a confidence indication of the determined initial sleep disordered breathing parameter using the sensed temperature information.

9. The implantable cardiac monitor of claim 8, wherein the confidence indication includes indications of high confidence and low confidence, and
- wherein the assessment circuit is configured to:
  - determine an indication of high confidence if the sensed temperature information corresponding to the determined initial sleep disordered breathing parameter is at or above a threshold; and
  - determine an indication of low confidence if the sensed temperature information corresponding to the determined initial sleep disordered breathing parameter is below the threshold.

10. A medical device system, comprising:
- a signal receiver circuit configured to receive respiration information of a patient and temperature information of an implantable housing of the medical device system; and
- an assessment circuit configured to determine distal skin temperature of the patient using the received temperature information and to determine a sleep disordered breathing parameter of the patient using the received respiration information and the determined distal skin temperature of the patient.

11. The medical device system of claim 10, wherein the respiration information comprises impedance information of the patient indicative of a tidal volume of the patient, and
- wherein the assessment circuit is configured to determine the sleep disordered breathing parameter using a detected decrease in the received impedance information greater than a sleep disordered breathing threshold from a baseline respiration measure over a detection window.

12. The medical device system of claim 11, wherein the assessment circuit is configured to determine the sleep disordered breathing parameter using a combination of the received impedance information over the detection window and the temperature of the implantable housing corresponding to the detection window.

13. The medical device system of claim 12, wherein the assessment circuit is configured to determine the sleep disordered breathing parameter using the detected decrease in the received impedance information indicative of the tidal volume of the patient greater than the sleep disordered breathing threshold and the temperature of the implantable housing greater than a temperature threshold,
- wherein the sleep disordered breathing parameter includes an indication that a sleep disordered breathing event has occurred over the detection window, and
- wherein the assessment circuit is configured to determine the baseline tidal volume measure using the determined tidal volume measure of the patient over a baseline period longer than the detection window and preceding the detection window.

14. The medical device system of claim 13, wherein the detection window has a period between 5 and 15 seconds,
- wherein the baseline period is a minute or longer,
- wherein the assessment circuit is configured to count a number of sleep disordered breathing events in a daily period, and
- wherein the assessment circuit is configured to adjust at least one of the sleep disordered breathing threshold or the length of the detection window using the received temperature information.

15. The medical device system of claim 11, wherein the assessment circuit is configured to:
- determine an initial sleep disordered breathing parameter of the patient using the received respiration information; and
- determine a confidence indication of the determined initial sleep disordered breathing parameter using the received temperature information.

16. The medical device system of claim 15, wherein the confidence indication includes indications of high confidence and low confidence, and
- wherein the assessment circuit is configured to:
  - determine an indication of high confidence if the received temperature information corresponding to the determined initial sleep disordered breathing parameter is at or above a threshold; and
  - determine an indication of low confidence if the received temperature information corresponding to the determined initial sleep disordered breathing parameter is below the threshold.

17. A method, comprising:
- receiving respiration information of a patient and temperature information of an implantable housing of a medical device system using a signal receiver circuit; and
- determining, using an assessment circuit, distal skin temperature of the patient using the received temperature information and a sleep disordered breathing parameter of the patient using a combination of the received respiration information and the determined distal skin temperature of the patient.

18. The method of claim 17, wherein the respiration information comprises impedance information of the patient indicative of a tidal volume of the patient, and wherein determining the sleep disordered breathing parameter of the patient comprises using: (1) a detected decrease in the received impedance information greater than a sleep disordered breathing threshold from a baseline respiration measure over a detection window, and (2) the temperature of the implantable housing corresponding to the detection window.

19. The method of claim 18, wherein determining the sleep disordered breathing parameter includes determining an indication that a sleep disordered breathing event has occurred over the detection window, and wherein the method comprises:

determining the baseline respiration measure using the respiration information of the patient over a baseline period longer than and preceding the detection window;

counting a number of sleep disordered breathing events of the patient in a daily period; and adjusting at least one of the sleep disordered breathing threshold or the length of the detection window using the received temperature information, wherein the detection window has a period between 5 and 15 seconds, and wherein the baseline period is a minute or longer.

20. The method of claim 18, wherein determining the sleep disordered breathing parameter comprises:

determining an initial sleep disordered breathing parameter of the patient using the received respiration information; and determining a confidence indication of the determined initial sleep disordered breathing parameter using the received temperature information.

21. An implantable cardiac monitor, comprising:

a respiration sensor configured to sense respiration information of a patient;

a temperature sensor configured to sense temperature information of the patient; and an assessment circuit configured to determine a sleep disordered breathing parameter of the patient using the sensed respiration information of the patient and the sensed temperature information of the patient, wherein, to determine the sleep disordered breathing parameter, the assessment circuit is configured to:

determine an initial sleep disordered breathing parameter of the patient using the sensed respiration information; and determine a confidence indication of the determined initial sleep disordered breathing parameter using the sensed temperature information.

22. The implantable cardiac monitor of claim 21, wherein the confidence indication includes indications of high confidence and low confidence, and wherein the assessment circuit is configured to:

determine an indication of high confidence if the sensed temperature information corresponding to the determined initial sleep disordered breathing parameter is at or above a threshold; and determine an indication of low confidence if the sensed temperature information corresponding to the determined initial sleep disordered breathing parameter is below the threshold.

* * * * *